(12) United States Patent
Wilson et al.

(10) Patent No.: US 10,010,241 B2
(45) Date of Patent: Jul. 3, 2018

(54) CAPSULE ORIENTATION DETECTION FOR CAPSULE DOCKING SYSTEM WITH INDUCTIVE POWER DRIVE CIRCUIT

(71) Applicant: Capso Vision, Inc., Saratoga, CA (US)

(72) Inventors: Gordon C Wilson, San Francisco, CA (US); Jiafu Luo, Irvine, CA (US); Kang-Huai Wang, Saratoga, CA (US); Chung-Ta Lee, Sunnyvale, CA (US); James Blanc, Incline Village, NV (US)

(73) Assignee: CAPSOVISION INC, Saratoga, CA (US)

( * ) Notice: Subject to any disclaimer, the term of this patent is extended or adjusted under 35 U.S.C. 154(b) by 970 days.

(21) Appl. No.: 14/341,702

(22) Filed: Jul. 25, 2014

(65) Prior Publication Data

US 2014/0364688 A1 Dec. 11, 2014

Related U.S. Application Data

(63) Continuation-in-part of application No. PCT/US2013/039317, filed on May 2, 2013.

(Continued)

(51) Int. Cl.
*A61B 1/00* (2006.01)
*A61B 1/04* (2006.01)
*A61B 5/07* (2006.01)

(52) U.S. Cl.
CPC ...... *A61B 1/00013* (2013.01); *A61B 1/00006* (2013.01); *A61B 1/00016* (2013.01);

(Continued)

(58) Field of Classification Search
CPC ... A61B 1/041; A61B 1/00057; A61B 1/0011; A61B 1/00142; A61B 1/00144;

(Continued)

(56) References Cited

U.S. PATENT DOCUMENTS 7,558,620 B2 * 7/2009 Ishibashi ............ A61B 1/00016
128/903
7,766,167 B2 * 8/2010 Segawa .............. A61B 1/00144
206/363

(Continued)

OTHER PUBLICATIONS

Siamak Bastami, et al., "Magnetic Induction or Magnetic Resonance forWireless Charging?" Bodo's Power Systems, pp. 22-26, Jan. 2013, ISSN: 1863-5598.

(Continued)

*Primary Examiner* — John P Leubecker
*Assistant Examiner* — Arnaldo Torres Diaz
(74) *Attorney, Agent, or Firm* — Blairtech Solution LLC

(57) ABSTRACT

A capsule endoscopic system is disclosed for receiving data from a capsule device and providing inductive power to the capsule device wirelessly, where the capsule endoscopic system incorporates a feature to automatically protect the capsule device and the docking device from damage if the capsule device is docked in a backward orientation. In one embodiment, the docking device comprises a current sense circuit to detect the current flowing through the primary coil or primary drive circuit. The occurrence of wrong orientation can be detected from the current. A detection/control circuit can be used to provide the needed control in order to prevent damage to the system. In another embodiment, a resonant circuit comprising a capacitor and the primary coil is used to provide the needed protection when the capsule device is docked with a wrong orientation.

10 Claims, 9 Drawing Sheets

Related U.S. Application Data

(60) Provisional application No. 61/649,238, filed on May 19, 2012.

(52) U.S. Cl.
CPC ...... *A61B 1/00029* (2013.01); *A61B 1/00032* (2013.01); *A61B 1/00034* (2013.01); *A61B 1/00055* (2013.01); *A61B 1/00144* (2013.01); *A61B 1/00158* (2013.01); *A61B 1/041* (2013.01); *A61B 5/073* (2013.01); *A61B 2560/0204* (2013.01); *A61B 2560/0456* (2013.01)

(58) Field of Classification Search
CPC ....... A61B 1/00147; A61B 1/01; A61B 1/051; A61B 1/053; A61B 1/055; A61B 5/6861; A61B 2562/162; A61B 1/00027; A61B 1/00029; A61B 2560/0456; G02B 23/2476
See application file for complete search history.

(56) References Cited

U.S. PATENT DOCUMENTS

| | | | | |
|---|---|---|---|---|
| 7,770,725 B2* | 8/2010 | Segawa | ............. | A61B 1/00144 206/363 |
| 7,775,971 B2* | 8/2010 | Fujimori | ................. | A61B 1/04 600/110 |
| 7,850,006 B2* | 12/2010 | Uchiyama | .......... | A61B 1/00144 206/350 |
| 7,931,149 B2* | 4/2011 | Gilad | ................. | A61B 1/00144 206/477 |
| 7,998,059 B2* | 8/2011 | Fujimori | ............... | A61B 1/041 348/340 |
| 8,073,223 B2* | 12/2011 | Wilson | ............... | A61B 1/00009 348/699 |
| 8,089,508 B2* | 1/2012 | Yokoi | ................ | A61B 1/00016 348/64 |
| 8,128,560 B2* | 3/2012 | Segawa | ............. | A61B 1/00144 600/15 |
| 8,343,038 B2* | 1/2013 | Segawa | ............. | A61B 1/00036 600/109 |
| 8,454,495 B2* | 6/2013 | Kawano | ............. | A61B 1/00036 600/103 |
| 8,790,248 B2* | 7/2014 | Uchiyama | .......... | A61B 1/00036 600/117 |
| 8,915,840 B2* | 12/2014 | Sato | ................... | A61B 1/00016 307/104 |
| 2004/0254455 A1* | 12/2004 | Iddan | ................. | A61B 1/00144 600/424 |
| 2007/0098379 A1* | 5/2007 | Wang | ................. | A61B 1/00009 396/14 |
| 2008/0027267 A1* | 1/2008 | Segawa | ............. | A61B 1/00144 600/7 |
| 2008/0039675 A1* | 2/2008 | Segawa | ............. | A61B 1/00144 600/7 |
| 2008/0167523 A1* | 7/2008 | Uchiyama | .......... | A61B 1/00036 600/114 |
| 2008/0257768 A1* | 10/2008 | Uchiyama | .......... | A61B 1/00144 206/350 |
| 2009/0163771 A1* | 6/2009 | Kimoto | ............. | A61B 1/00016 600/118 |
| 2011/0218402 A1* | 9/2011 | Sato | ................... | A61B 1/00016 600/160 |
| 2012/0007973 A1* | 1/2012 | Tsutsumi | ........... | A61B 1/00016 348/65 |
| 2012/0080351 A1* | 4/2012 | Takahashi | .......... | A61B 1/00144 206/528 |

OTHER PUBLICATIONS

Neil Kuyvenhoven, et al., "Development of a Foreign Object Detection and Analysis Method for Wireless Power Systems", 2011 IEEE Symposium on Product Compliance Engineering (PSES), Oct. 10-12, 2011, pp. 1-6.

* cited by examiner

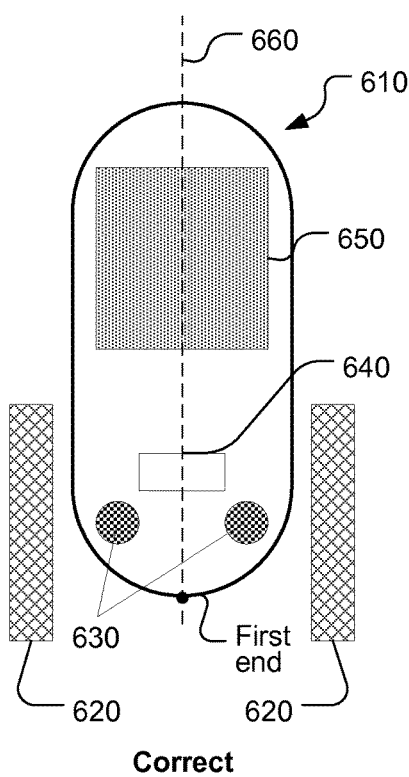 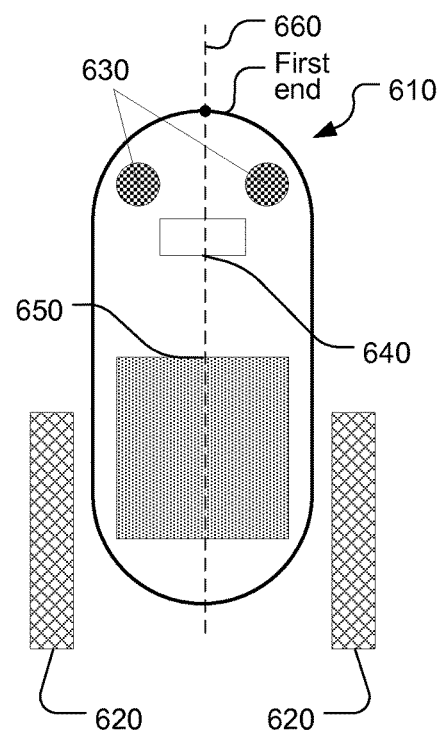
Correct orientation     Incorrect orientation
*Fig. 6A*     *Fig. 6B*

CAPSULE ORIENTATION DETECTION FOR CAPSULE DOCKING SYSTEM WITH INDUCTIVE POWER DRIVE CIRCUIT

CROSS REFERENCE TO RELATED APPLICATIONS

The present invention is a continuation-in-part of and claims priority to PCT Patent Application, Serial No. PCT/US13/39317, filed on May 2, 2013, which claims priority to U.S. Provisional Patent Application No. 61/649,238, filed on May 19, 2012. The PCT Patent Application and the U.S. Provisional Patent Application are hereby incorporated by reference in their entireties.

FIELD OF THE INVENTION

The present invention relates to accessing recorded data from a capsule device using a docking system with inductive power drive circuit. In particular, the present invention relates to detecting orientation of the capsule device when the capsule device is placed in the docking station.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. Alternatively, the endoscope might record an image electronically at the distal end, for example using a CCD or CMOS array, and transfer the image data as an electrical signal to the proximal end through a cable. Because of the difficulty traversing a convoluted passage, endoscopes cannot easily reach the majority of the small intestine and special techniques and precautions, that add cost, are required to reach its entirety. The cecum and ascending colon also require significant effort and skill to reach with an endoscope. An alternative in vivo image sensor that addresses many of these problems is a capsule endoscope. A camera is housed in a swallowable capsule, along with a radio transmitter for transmitting data, primarily comprising images recorded by the digital camera, to a base-station receiver or transceiver and data recorder outside the body. Another autonomous capsule camera system with on-board data storage was disclosed in the U.S. patent application Ser. No. 11/533,304, filed on Sep. 19, 2006.

For the above in vivo devices, a large amount of image data is collected traversing through a lumen in the human body such as the gastrointestinal (GI) tract. The images captured, along with other information, are stored in the on-board archival memory inside the capsule camera. The archival memory may come in various forms of non-volatile memories. After the capsule camera exits from the anus, it is retrieved to recover the data stored on-board. In a conventional approach, it would require a fairly expensive data access system that includes opening the capsule and docking to it. Because of the requirement to open the capsule and align contact pins to pads in the capsule, some degree of mechanical complexity is inevitable. Therefore, such tasks usually are performed by specially trained persons. In PCT Patent Application, Serial No. PCT/US13/39317, filed on May 2, 2013, a docking system is disclosed, which can access data from the capsule device wirelessly. The docking system is also referred as a docking station in this disclosure. Furthermore, the docking system also provides power to the capsule device externally using inductive drive circuits.

However, the arrangement disclosed in PCT Patent Application, Serial No. PCT/US13/39317, filed on May 2, 2013 is prone to human error when the capsule device is placed into the docking system. The housing of the capsule device is typically made symmetrical in shape. Therefore, the capsule device may be incidentally placed into the docking system with a wrong orientation, which may cause the inductive power drive circuit to function improperly or even cause damage to the capsule device or the docking system. It is desirable to design a protective apparatus for the docking system to prevent any damage to the capsule device or the docking system in case that the capsule device is placed into the docking system with a wrong orientation. Also, it is desirable that the apparatus is capable of providing indication or warning to alert a user/technician regarding the occurrence of wrong orientation.

BRIEF SUMMARY OF THE INVENTION

A capsule endoscopic system is disclosed for receiving data from a capsule device and providing inductive power to the capsule device wirelessly. In one embodiment, the system comprises a capsule device and a docking device. The capsule device comprises a secondary coil, one or more battery and a capsule housing, where the secondary coil and the batteries are sealed in the capsule housing. The docking device comprises a primary coil, a primary drive circuit and a current sense circuit. The primary coil generates an alternating magnetic field, where the magnetic field is coupled to the secondary coil to supply power to the capsule device wirelessly when the capsule device is docked in the docking device with a correct orientation with the secondary coil inside or proximal to the primary coil. The primary drive circuit is coupled to the primary coil to provide an AC (alternating current) signal to the primary coil for generating the alternating magnetic field. The current sense circuit is coupled to the primary drive circuit or the primary coil to measure first current flowing through the primary drive circuit or the primary coil. An error signal is then generated based on the first current when the capsule device is docked in a wrong orientation.

The docking device may further comprise a detection/control circuit coupled to the current sense circuit and the error signal is generated based on the first current using the detection/control circuit when the capsule device is docked in the wrong orientation. The detection/control circuit can be further configured to provide first control to the primary drive circuit to prevent or reduce damage to the capsule device, the docking device, or both when the error signal is asserted. To prevent or reduce the damage, the first control can cause the primary drive circuit to be disconnected from the primary coil or from a power supply that provides power to the primary drive circuit, or cause the primary drive circuit to reduce a primary voltage across the primary coil or a duty cycle of the AC signal. The detection/control circuit may also be configured to provide a warning signal, an indication of assertion of the error signal, a message, or a combination thereof when the error signal is asserted. The detection/control circuit can be a hardware-based implementation to provide high level of reliability.

The capsule device may further comprise an archival memory to store first data captured inside a body lumen by the capsule device and a wireless transmitter to transmit the first data, the docking device further comprises a wireless receiver to receive the first data from the capsule device, where the archival memory and the wireless transmitter are also sealed in the capsule housing. The wireless transmitter and the wireless receiver may correspond to an optical transmitter and an optical receiver respectively. The wireless transmitter can be located proximal to a same end of the capsule device as the secondary coil. The capsule device may also further comprise a camera to capture images inside a body lumen, where the camera is enclosed in the capsule housing.

While a detection/control circuit can be used, the docking device may also use a central processing unit (CPU) or a controller to generate the error signal based on the first current when the capsule device is docked in the wrong orientation. The CPU or the controller can also be configured to provide first control to the primary drive circuit to prevent or reduce the damage to the capsule device, the docking device, or both when the error signal is asserted.

In yet another embodiment of the present invent, a resonant circuit comprising a capacitor and the primary coil is used to provide the needed protection when the capsule device is docked with a wrong orientation. The resonant circuit has a corresponding quality factor and a resonant frequency. When the capsule device is docked in a correct orientation, the resonant circuit exhibits a high quality factor. When the capsule device is docked in a wrong orientation, the frequency response curve will be broadened and the quality factor will be lowered. The lowered quality factor will cause reduced voltage across the primary coil and the secondary coil. Accordingly, the capsule device and the docking device will be protected from damage due to wrong orientation. Alternatively, a voltage sense circuit may be used in this case to detect the occurrence of wrong orientation. A detection/control circuit may be used to generate an error signal when a wrong orientation is detected and provide necessary control signal to protect the docking device, the capsule device or both.

BRIEF DESCRIPTION OF THE DRAWINGS

FIGS. 6A-B illustrates two different situations that the capsule device is placed in the docking system, where FIG. 6A illustrates that the capsule device is placed in a correct orientation and FIG. 6B illustrates that the capsule device is placed in the docking system in a wrong orientation.

FIG. 8A illustrates an example of primary drive based on a resonant circuit, FIG. 8B illustrates a system including an additional voltage sense circuit, and FIG. 8C illustrates a system further including a detection/control circuit.

DETAILED DESCRIPTION OF THE INVENTION

Figure 1:
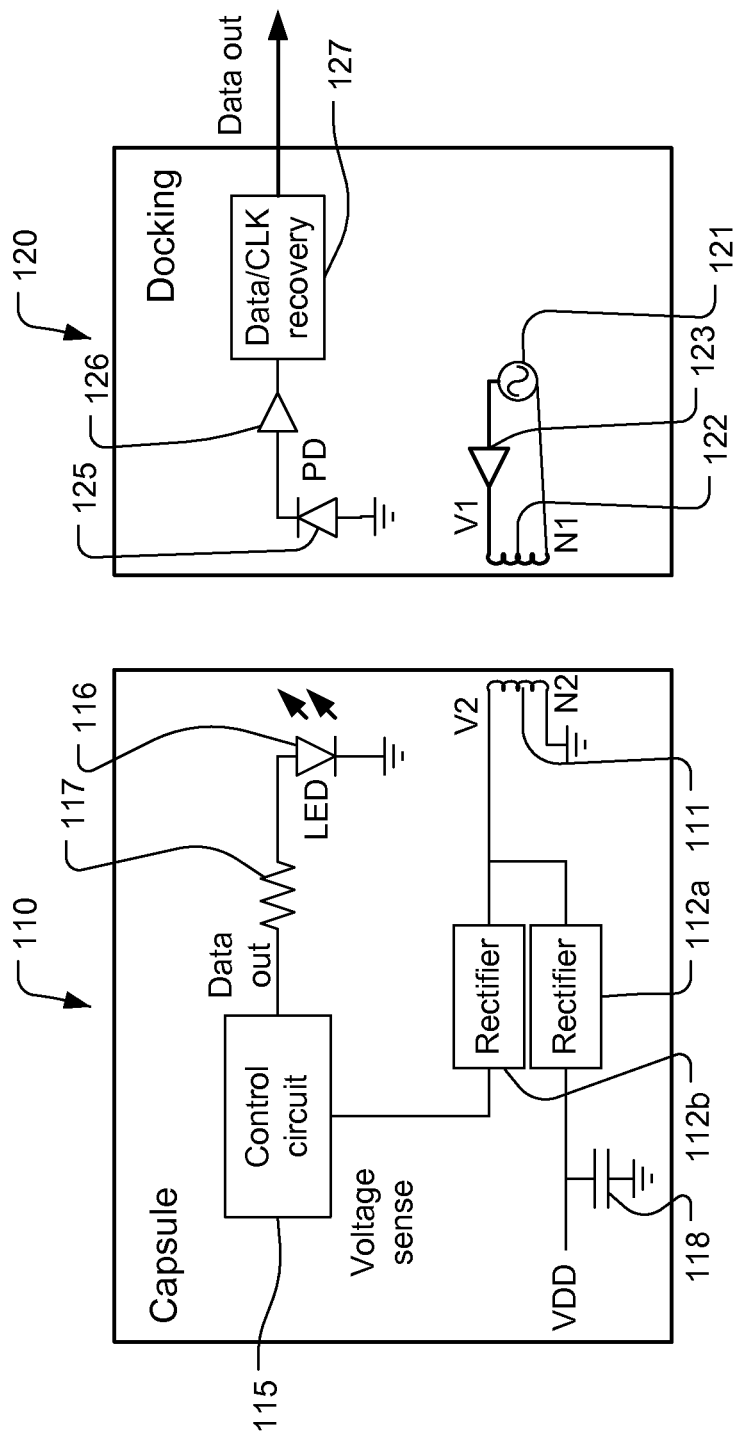
FIG. 1 illustrates an example of system architecture of an optical wireless docking system according to the present invention.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

In order to overcome the shortcomings in a conventional docking system, an optical wireless docking system according to the present invention has disclosed in PCT Patent Application, Serial No. PCT/US13/39317, filed on May 2, 2013 by some common inventors. The wireless docking system allows data downloading from the capsule device without the need of opening the device or aligning the device precisely. After the capsule camera exits from the anus, the battery or batteries inside are likely depleted or nearly depleted. Therefore, the docking system according to PCT/US13/39317 supplies power to the capsule from outside of the capsule device. In one embodiment, magnetic induction has been disclosed as a means for providing the power to the capsule device externally. Furthermore, the docking system according to PCT/US13/39317 allows data stored inside the capsule device to be transmitted wirelessly, such as by an optical or radio means.

In one embodiment according to PCT/US13/39317, the docking system utilizes inductive powering and optical transmission. Nevertheless, radio transmission may also be used to practice the present invention. Any optical source requiring very little space to fit into the capsule may be considered. The optical source should be able to support fast data transmission. The amount of data stored in a capsule camera may be as much as 500 Mbytes and the data size will continue to grow along with the trend of high-resolution demand. If 1 Mbps (million bits per second) transmission speed is supported, it may take around 100 minutes to read out 500 Mbytes data if overhead in data transmission protocol is taken into account. Therefore, it is preferably to select an optical source that can support higher data rate. As one example, the optical source can be a directly modulated LED or Vertical-Cavity Surface-Emitting Laser diode (VCSEL) with a target bit rate of 10 Mbps.

Exemplary system architecture is shown in FIG. 1, where LED 116 is used as a light source and a Photo Diode (PD) 125 is used as the receiver. Control circuit 115 is shown inside capsule camera 110. Control circuit 115 will read data stored in the archival memory (not shown) and process the retrieved data so that the data can be properly transmitted by light source 116. Light emitted from light source 116 will travel through the transparent window (not explicitly shown) of the capsule camera. The light from light source 116 will be received by a light receiving device such as photo diode 125 at docking system 120. The received signal will be properly amplified by amplifier 126. The amplified signal is then processed by receiver circuit 127 where data and clock will be recovered. The data recovered can be stored on a media such as a flash drive or computer hard disk drive. Alternatively, the data recovered may be provided to a workstation or a display station for further processing or viewing.

The output buffer from control circuit 115 will provide needed power for light source 116. For example, 5 mA current may be provided, which should be adequate to drive either an LED or VCSEL. The LED wavelength may be in the near Infrared (NIR), for example at 830 nm. Other LED wavelengths may also be used to practice the present invention. With a 3V drive voltage, the correct drive current is produced with series resistance 117. A bit rate of 10 Mbps or more can be achieved.

The receiver consists of photodiode 125, trans-impedance amplifier 126, and data/clock recovery module 127. This module could be implemented using a limiting amplifier and a PLL. However, this functionality could be performed digitally by sampling the waveform and using DSP to recover data and clock. The use of a UART might obviate the need for clock recovery. The interface protocol may be used for the intended operation around 10 Mbps frequency range. Other standard digital data interfaces may also be used. In FIG. 1, an optical link is shown as a wireless link between the capsule device and the docking device; a radio frequency (RF) link may also be used as the wireless link.

Inductive coupling relies on the mutual inductance between a primary coil outside the capsule and a secondary coil inside the capsule. The primary is driven by a sinusoidal voltage, and the secondary signal is rectified to produce a DC voltage. Exemplary system architecture is shown in FIG. 1. The system comprises capsule camera 110 and docking system 120. The inductive power is supplied from docking system 120 to capsule camera 110 through coupling coils 122 and 111. Coil 122 at the docking system side is referred to as primary side and coil 111 on the capsule camera side is referred to as the secondary side. At the primary side, signal source 121 provides the driving signal to primary coil 122. While a sinusoidal driving signal is shown, other alternating signals such as square wave or triangular wave may also be used. The driving signal from signal source 121 may be amplified by amplifier 123. Various other known means of producing an alternating current may be utilized to drive the primary. The voltage across primary coil 122 is named primary voltage V1 and the voltage across secondary coil 111 is named secondary voltage V2. It is well known in the art that the induced alternating voltage at the secondary side can be converted into a DC voltage to be used by the circuits inside the capsule camera. Rectifiers are often used for converting AC power to DC power. Two rectifiers 112$a$ and 112$b$ are shown in FIG. 1 to provide different DC outputs as required by the capsule camera. Furthermore, the circuits in the capsule device can be configured to charge rechargeable batteries inside the capsule device when the capsule device is docked in the docking device. For example, battery 118 may be a rechargeable battery and can be charged by the voltage output from rectifier 112$a$. Depending on the capsule camera design, it may require more or fewer voltage outputs. The rectifiers may also be integrated into a package or a module. The rectifier may be followed by a simple regulator, such as a Zener-diode circuit or other voltage control circuits. This provides more stability in the secondary voltage. Additionally, the rectifier may include voltage multiplication with a Greinacher, a Cockcroft-Walton, or other circuit. The components are selected to minimize the volume in order to fit into the limited space available inside the capsule camera. A voltage multiplier allows a smaller and lighter secondary coil to be used but requires additional diodes and capacitors.

The ratio of the secondary to primary voltage is:

$$\frac{V_2}{V_1} = \beta \frac{N_2}{N_1}, \quad (1)$$

where $N_2$ is the number of secondary coil turns, $N_1$ is the number of primary coil turns. The coupling coefficient is the ratio of the coil fluxes:

$$\beta = \frac{\phi_2}{\phi_1}. \quad (2)$$

The flux through a coil is given by integration of the flux density through a surface defined by the coil perimeter $$\phi_i = \int_S B_i \cdot dS_i. \quad (3)$$

The coupling coefficient β can be increased by making the secondary coil area larger and by designing pole pieces for the primary and/or secondary that concentrate the magnetic flux. For sinusoidal modulation of the primary at frequency f, the flux amplitude in the primary and secondary is given by $$\phi_i = \frac{V_i}{\sqrt{2}\pi f N_i} \quad (4)$$

Figure 2A:
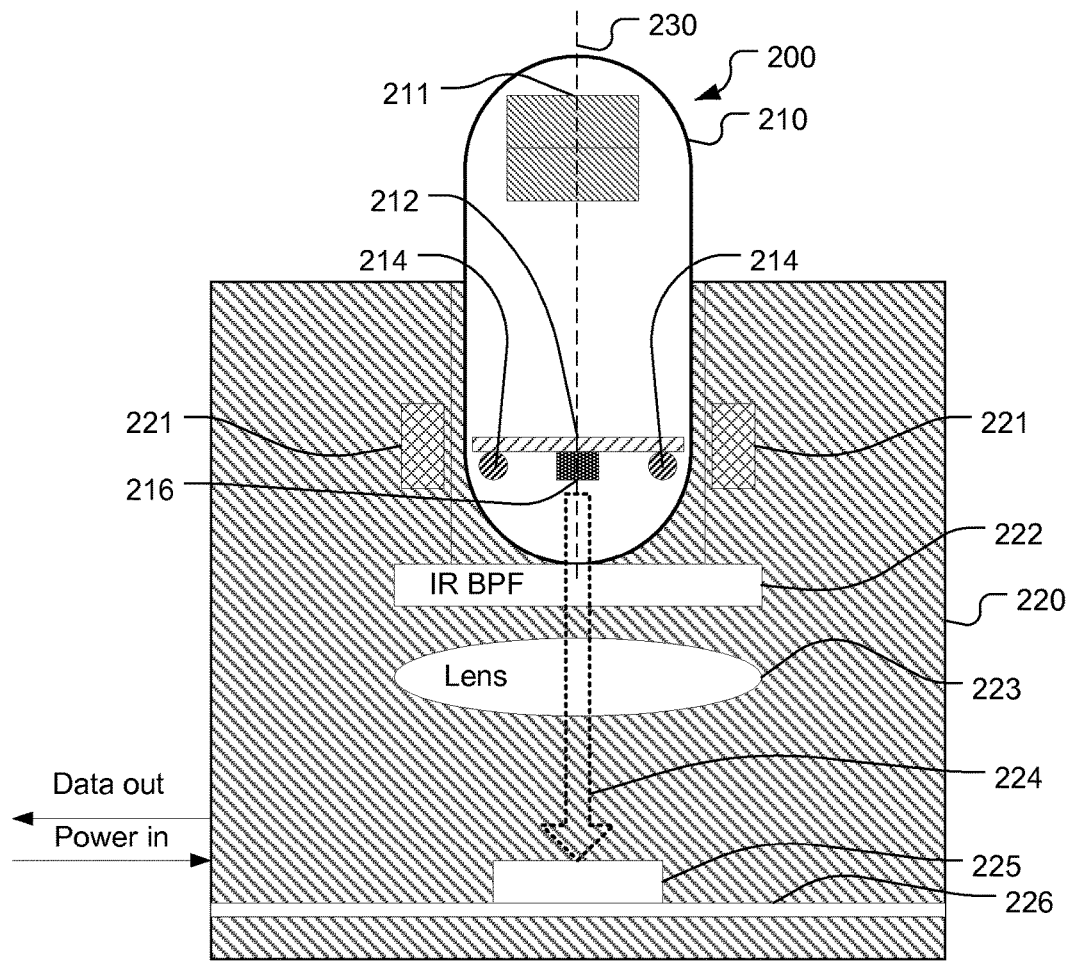
FIGS. 2A-B illustrate an exemplary optical wireless docking system according to the present invention, where the system is configured with longitudinal-field geometry.
Figure 2B:
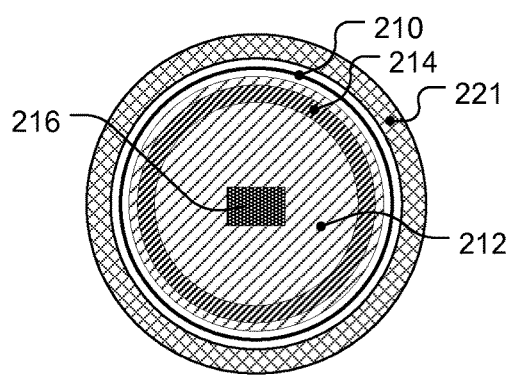

As mentioned before, the secondary coil is located inside the capsule camera. In order to properly couple the electromagnetic field from the primary coil to the secondary coil, the two coils have to be correctly positioned and aligned. On the other hand, in order to read out data from the capsule camera optically, light passage has to be provided between the light source and the light detector. Accordingly, one exemplary system configuration to provide light passage as well as magnetic field coupling is shown in cross section in FIGS. 2A and 2B, where FIG. 2B represents a bottom view of the capsule camera. The type of arrangement is called longitudinal-field geometry.

Primary coil 221 wraps around the capsule housing 210 of capsule 200. Secondary coil 214 is on the perimeter of bottom PCB 212 in the capsule. Primary coil 221 and secondary coil 214 should be centered on the same plane. Secondary coil 221 can also be implemented as a printed circuit as a spiral on multiple layers of PCB 212, although the practical pitch of the traces limits the number of turns. Alternatively, a coil can be produced with thin-gauge insulated wires held in shape with shellac and mounted to the PCB as a through-hole or surface mount component.

Light source 216 (LED or VCSEL) sits on the center of the board facing down. Batteries 211 are located at the other end of the capsule camera so that the batteries will not block light passage 224 from the light source to the light receiver. Lens 223 may be used to focus the light onto light receiver 225 such as a photodiode. Optional Band Pass Filter (BPF) 222 for the light can be installed in light passage 224 between light source 216 and light receiver 225. The components including the primary coil 221, the light BPF 222, the lens 223, the light receiver 225 and associated Printed Circuit Board 226 are housed in the docking system 220. The arrangement is symmetrical so that the rotational orientation of the capsule is not significant to the inductive coupling or the received optical power. A disadvantage is that eddy currents will be induced in the traces and power planes on PCB 212 itself. These currents can cause heating and also induce unwanted signals into the capsule circuits, which are henceforth referred to as "noise." In the worst case, where a circuit trace forms a loop around the PCB, the induced voltage in the trace is $V_2/N_2$. Increasing the number of secondary turns will decrease this noise but increase the volume occupied by the secondary coil. The noise can also be limited by minimizing the loop area of traces in the capsule PCB.

Figure 3:
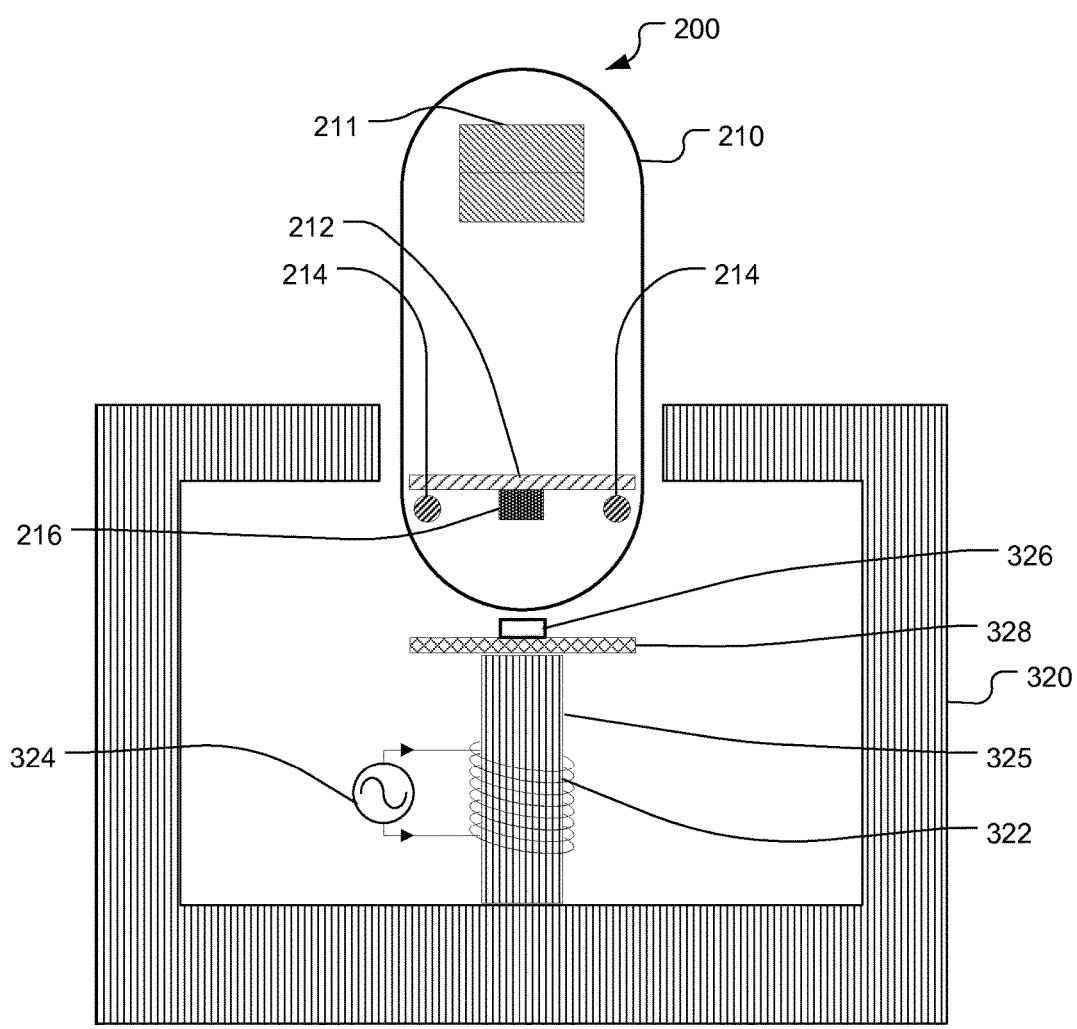
FIG. 3 illustrates an exemplary optical wireless docking system according to the present invention, where the system is configured with alternative longitudinal-field geometry.
Figure 4:
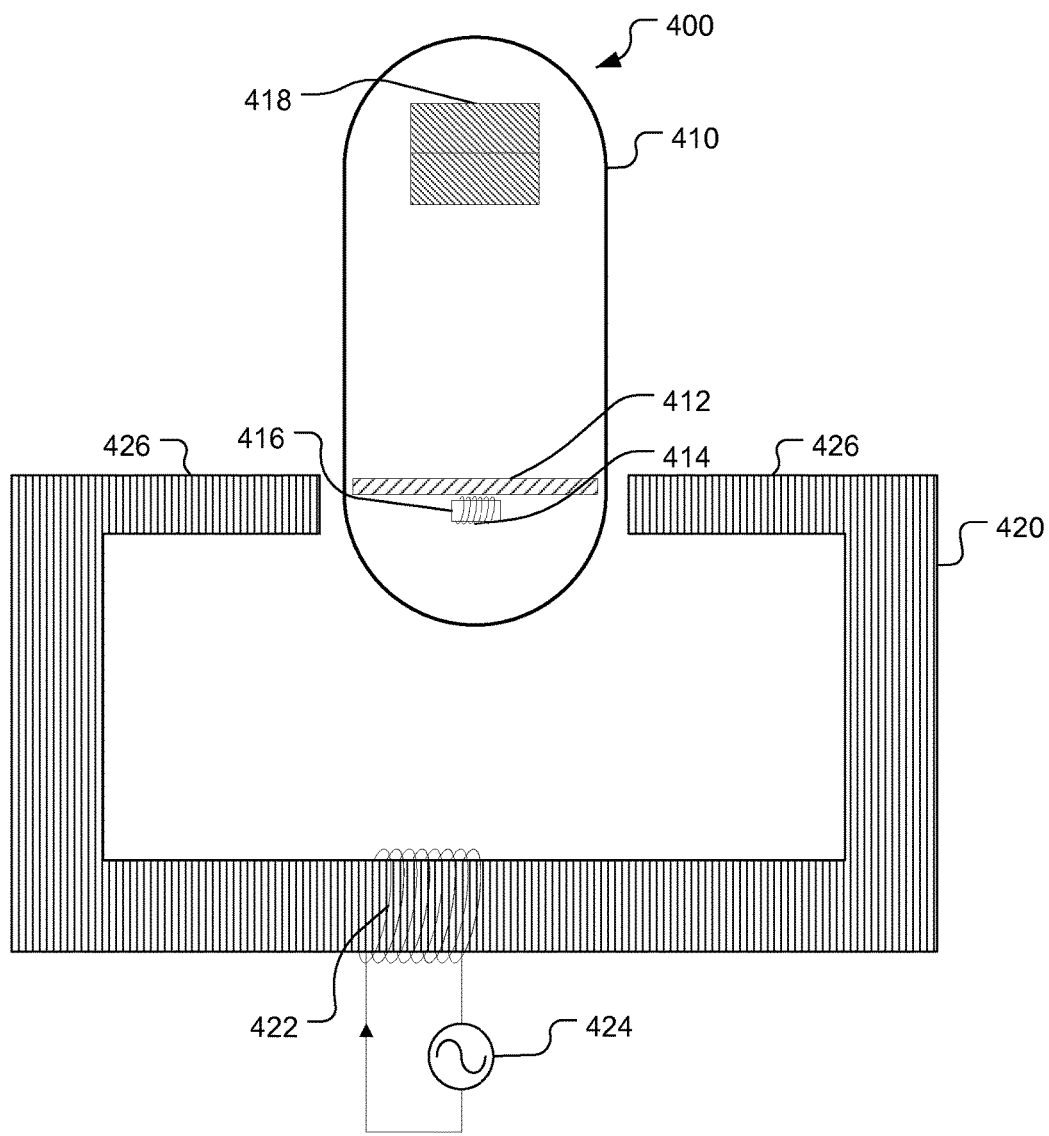
FIG. 4 illustrates an exemplary optical wireless docking system according to the present invention, where the system is configured with lateral-field geometry.
Figure 5:
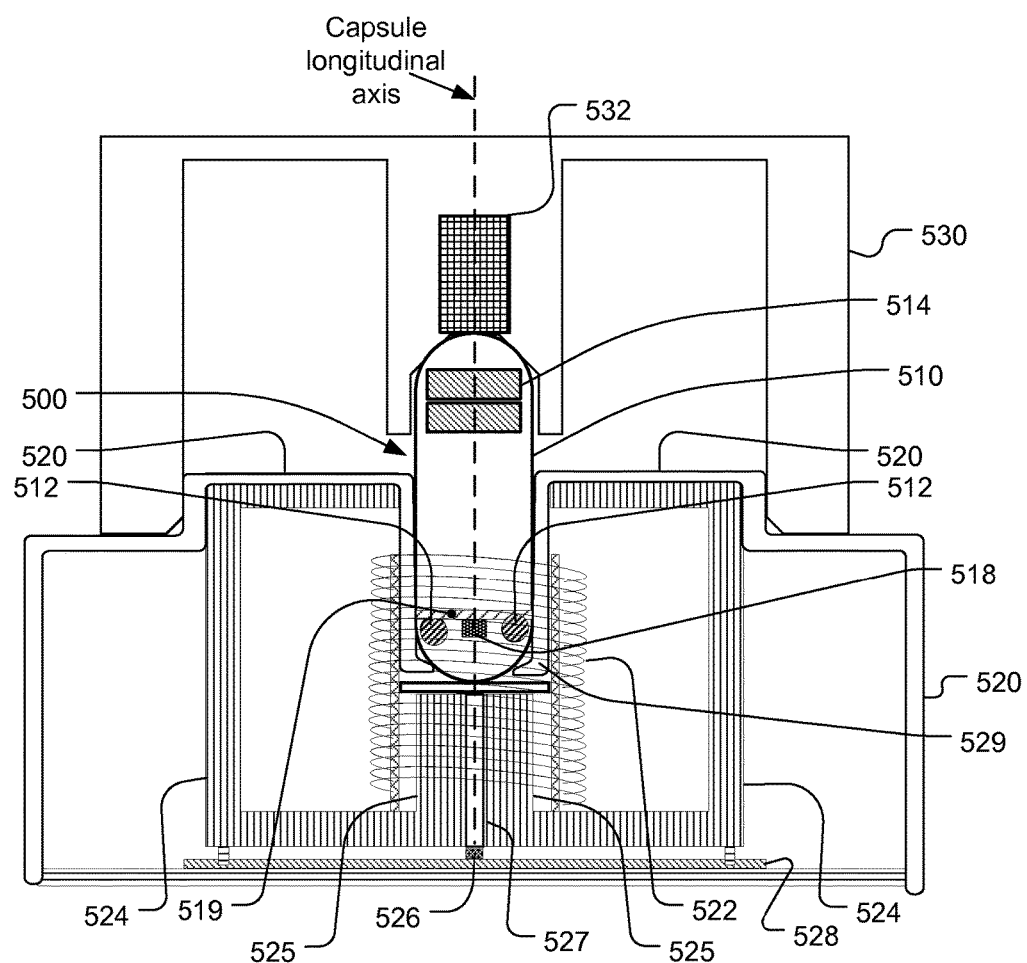
FIG. 5 illustrates a cross-section view of an exemplary optical wireless docking system according to the present invention, where the system is configured with longitudinal-field geometry.

Other embodiments of the docking system have also been disclosed in PCT/US13/39317 to address various issues. For example, a ferrite core for the primary coil on the primary side can be used to reduce the magnetic flux reaching the batteries as shown in FIG. 3. In another embodiment, the problem of spurious eddy currents is reduced by orienting the field horizontally to PCB and batteries so that the primary coil and secondary coil are arranged in lateral-field geometry as shown in FIG. 4. The secondary coil may also be wrapped around a ferrite. FIG. 5 illustrates another arrangement, where a docking bay is used to receive the capsule device. A portion of the capsule device is surrounded by the primary coil to increase the magnetic flux coupled to the secondary coil. Furthermore, a lid for the docking system is used as shown in FIG. 5.

FIG. 3 illustrates another primary coil arrangement where ferrite core 320 for the primary coil on the primary side can reduce the magnetic flux reaching the batteries. The ferrite core 320 is also referred to as a primary core in this disclosure. The primary core may have a shell structure to enclose the primary coil. The shell has an opening to allow the capsule device to be docked through the opening. The primary core may be a ferrimagnetic material or may be a ferromagnetic material such as steel. A ferrite has the advantage of low electrical conductivity and, as a result, low eddy current loss. Coin-cell silver oxide or lithium batteries have high energy density and a round package that fits well in a capsule, but these generally have steel cases that could be inductively heated, creating the potential for battery bursting. The core also will reduce the field emitted by the system, which might be an issue for electromagnetic compatibility (EMC) requirement compliance. Photodiode 326, mounted on PCB 328, sits above post piece 325. Primary coil 322 is wrapped around post piece 325. Signal source 324 provides driving signal to primary coil 322. This design has no lens, but uses VCSEL 216, which has an output beam with much lower divergence than an LED.

The problem of spurious eddy currents can be reduced by orienting the field horizontally to the PCB and batteries, as shown in FIG. 4. The arrangement between the primary coil and secondary coil is named lateral-field geometry. Small coil 414 wrapped around ferrite 416 is placed on PCB 412 aligned to the post pieces 426. Capsule 400 with housing 410 must be oriented to post pieces 426. β is reduced relative to the geometry of FIG. 2A because of the small area of secondary coil 414. On the other hand, ferrite core 416 will concentrate the field lines within secondary coil 414 to some degree. This effect is maximized if the gap between the post pieces is minimized and the length of the ferrite 416 is maximized. However, the length is limited by the available space in the capsule. Primary coil 422 is wrapped around primary core 420 and is driven by driving signal 424. While a C-shaped primary core is used, a toroidal-shaped structure or other geometry can also be used.

The capsule can be inserted into an opening in the system housing. At the bottom of the hole is a window, where a band pass filter at the LED wavelength can be placed. A lens may be used to focus the emitted light onto the photodiode. FIG. 5 illustrates an exemplary optical wireless docking system according to the present invention. The components for the docking device side can be placed inside the docking device housing. The exemplary docking system in FIG. 5 consists of base part 520 and holder part or cover part 530. Holder/cover part 530 can be pulled open or separated from the base part to insert or remove capsule 510. Secondary coil 512 inside the capsule and primary coil 522 are configured longitudinally. Part of the primary coil is wrapped around center post 525 of primary ferrite 524 (or primary core).

The primary ferrite has a shell-shaped structure to provide passage 527 between light source 518 inside capsule 500 and light receiver 526. A bore in the center of the post serves as the passage. Light source 518 may be mounted on circuit board 519 within capsule housing 510, where other circuits for the capsule camera may also be mounted on the board. Light receiver 526 may be mounted on PCB 528 where other circuits for the docking system can be implemented. The bore in the post is aligned with the longitudinal axis of the capsule device to allow light emitted from the light source 518 to pass through the light passage to reach light receiver 526. The capsule device is shown partially into the inner surface of the shell (i.e., primary core 524) so that the batteries remain outside the shell to reduce the influence of the magnetic flux on the batteries. A recessed structure (529) is formed in the center of the base part (520) of the docking device and is used as a receptacle for the capsule device.

The capsule retrieved after it exits from the anus may still have some remaining battery power, which may prevent the capsule circuits from resetting properly. In order to ensure proper data retrieval operation, an internal power off switch under the control of an external magnetic field is applied. Accordingly, magnet 532 is incorporated in holder/cover part 530. When the hold/cover is at a closed position, the internal switch will be under the influence of the magnetic force to cause the batteries to be disconnected from the capsule circuits.

In general, the secondary coil is located close to one end of the capsule device in the longitudinal direction (230) as shown in FIG. 2. The other end may have components containing bulk conductive material such as the battery or batteries, which have conductive steel cases. When the capsule is docked in the docking system correctly, as shown in FIG. 6A, the capsule device will be able to receive power inductively from the docking system. FIG. 6A illustrates a cross-section view of the capsule device (610) docked in the docking system, where only the primary coil (620) of the docking system is shown. The secondary coil (630) is located toward one end of the capsule device in the longitudinal direction (660). The end of the capsule device closer to the secondary coil (630) is designated as "first end" in this disclosure. When the capsule device is docked in the correct orientation, the electro-magnetic fields between the secondary coil (630) and the primary coil (620) are closely coupled. The capsule device also comprises components with electrically conductive bulk material (650) such as batteries. The components with electrically conductive bulk material (650) are usually located toward the other end of the capsule device in the longitudinal direction (660) to minimize the influence by the magnetic fields from the primary coil/secondary coil. The components with electrically conductive bulk material (650) are also abbreviated as conductive components in this disclosure. As mentioned before, the captured image data and/or other sensing data stored inside the capsule device can be downloaded wirelessly using a radio frequency (RF) link or an optical link.

Since the capsule device always has a symmetrical design, the operator may accidentally place the capsule backwards into the docking system. In this case, the conductive components (650) are situated within or located close to the primary coil while the secondary coil (630) in the capsule is outside the primary coil as shown as in FIG. 6B. With this wrong orientation, the capsule cannot be powered and the conductive components will be inductively heated, potentially creating a hazard. The battery or batteries might burst if they reach a high enough temperature (e.g., 100° C.), or a temperature could be reached which results in plastic melting and potentially a fire. Even if hazardous temperatures are not reached, the capsule may be damaged by excess heat so that the patient data cannot be downloaded even after the capsule orientation is corrected. Moreover, with the capsule backwards, the operator will know that the download is not working (the capsule will not be powered). However, he/she may not have any indication of the reason. Accordingly, the present invention discloses systems and methods for detecting the case that the capsule is placed into the docking system backward. Furthermore, by detecting the wrong capsule orientation, the present invention may activate protective procedures automatically, such as reducing the drive power, sending a control signal to the docking system CPU, or sending a message to the operator who can then reinsert the capsule with the correct orientation. A combination of these protective procedures may also be applied. The methods also prevent overheating a metal object, other than the capsule, that might fall into the docking system receptacle.

The capsule orientation could be sensed using a variety of sensors such as optical or inductive proximity sensors or cameras. However, there is little or no space inside or near the primary coil for a sensor, and the sensor itself could be inductively heated if it is in a region of high magnetic field. Potentially a sensor could be placed above the capsule outside the ferrite core (e.g., in a lid). For example, an inductive sensor might sense the presence of absence of the batteries in the top half of the capsule. However, this sensor could not detect the presence of a metal object that had fallen into the receptacle. Any such optical or inductive sensor also adds cost and complexity to the system.

Figure 7:
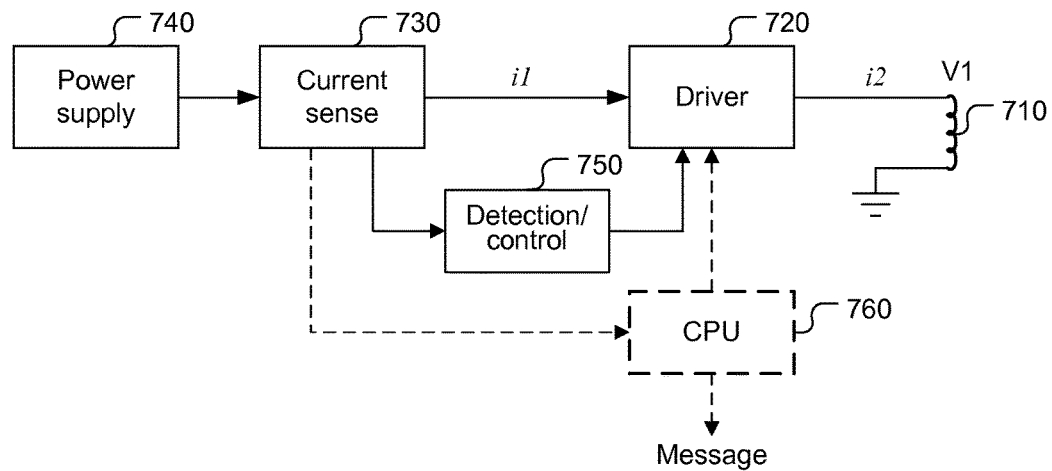
FIG. 7 illustrates an exemplary schematic of the docking system with an apparatus to protect the capsule and the system from damage due to wrong orientation according to one embodiment of the present invention.

A preferred sensing method according to the present invention is to detect change or changes to the state of the primary coil driver resulting from the presence of a conductive material in or near the primary coil. When the presence of a conductive material in or near the primary coil occurs, more power is dissipated in the conductive material than would normally be dissipated in the capsule electronics powered by the induced secondary voltage. Thus, the current delivered to the primary coil will be higher in the erroneous condition than in the normal condition. The current to the primary driver may be sensed as shown in the exemplary circuit of FIG. 7, where a current sense circuit (730) is coupled between the power supply (740) and the driver (720) to determine the current (i1) flowing into the driver of the primary coil (710). In FIG. 7, driver 720 is used to drive primary coil 710 by providing an alternating current (AC) such as square-wave, sine-wave signal or triangular wave. The current flowing into the drive provides an indication of the magnitude of the alternative current (i2) flowing into the primary coil. Alternatively, a current within the driver or the current into the primary coil may be sensed.

The current into the driver is typically a DC (direct current) current. One means of sensing it is to place a small current-sense resistor (e.g. 2 Ohms) in the path from the power supply to the driver. Additional circuitry measures the voltage across the resistor. If this voltage exceeds a reference voltage, an error signal indicating wrong capsule orientation is asserted using a detection/control module (750) that comprises a detection circuit such as a comparator. Alternatively, an inductive sensor could be used to sense the current. If the current at the input to the primary side is used for capsule orientation detection, this AC current might be detected by an inductive sensor or other standard means for detecting and measuring the current. The current sense circuits are well known in the field. Therefore, the details will not be discussed here.

A control signal can be generated and used to control the driver (720) in order to prevent or reduce potential damage that may be caused by wrong capsule orientation. For example, the control signal may then trigger a reduction in the drive voltage. It may open a switch, disconnecting the driver from the power supply or the primary from the driver; it may disable the driver; or it may change the state of the driver so that primary voltage is reduced. It may also reduce the duty cycle of the drive so that the primary voltage alternates between a high (e.g. nominal) and a lower (e.g. zero) voltage, thereby reducing power transfer to the conductive material. All these methods can be implemented in the hardware based detection/control circuit so that they do not rely on software or firmware control. This hardware-based solution will provide a high level of reliability.

The error signal may also be detected by using a CPU (760) to provide flexibility or programmability as shown in FIG. 7. Alternatively, the CPU may utilize the error signal generated by the detection/control circuit (750) to provide control to the drive (720). The CPU may also provide indication/warning/message. The indication/warning may be used to alert an operator visually or to cause an audible warning. The CPU may be based on the docking system CPU. In this case, the docking system CPU is used to provide the needed control function, message or indication as well. An individual CPU may also be used instead of the shared CPU to provide the needed control function, message or indication. While a CPU is shown in FIG. 7, an individual controller, microcontroller or digital signal processor may also be used to provide the needed control signals to the driver. The CPU can also disable the driver. Also, the CPU may also generate an error message to send to the operator or generate a warning signal to alert the operator. The message may include text displayed on a computer attached to the docking system (e.g. via a USB) and it may include messages displayed on the docking system itself. Furthermore, the needed detection/control function may also be implemented using a combination of the hardware-based control circuit and a CPU. In this case, it is preferred to use the docking system CPU to provide the needed control/warning/indication instead of a separate CPU to reduce cost. Therefore, the hardware based detection/control circuit can provide the high level of reliability and the CPU can provide flexibility and programmability.

Figure 8A:
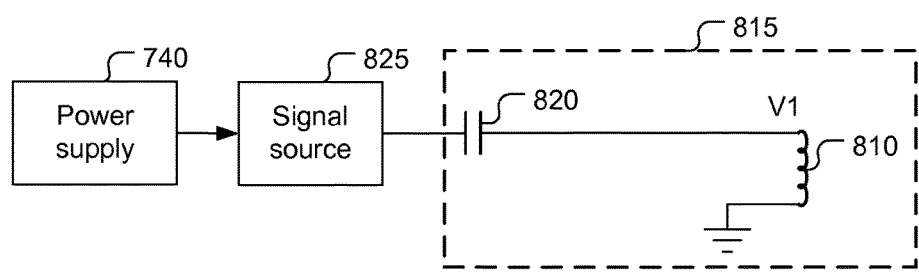
FIGS. 8A-C illustrate exemplary schematics of a docking system using a resonant circuit to protect the capsule and the system from damage due to wrong orientation according to another embodiment of the present invention, where

In another embodiment, the primary drive comprises a resonant circuit. FIG. 8A illustrates an example of primary drive based on a resonant circuit, where a capacitor (820) forms a resonant circuit (815) with the inductance of the primary coil (810). The resonant circuit has a corresponding resonant frequency and quality factor Q. A signal source (825) is coupled to the resonant circuit and a power supply (740) to provide the needed driving signal with a selected frequency. The selected frequency usually is at or near the resonant frequency. Typical resonant frequencies may be in the range for 50 kHz to 1000 kHz. For example, 225 kHz may be selected.

Figure 9:
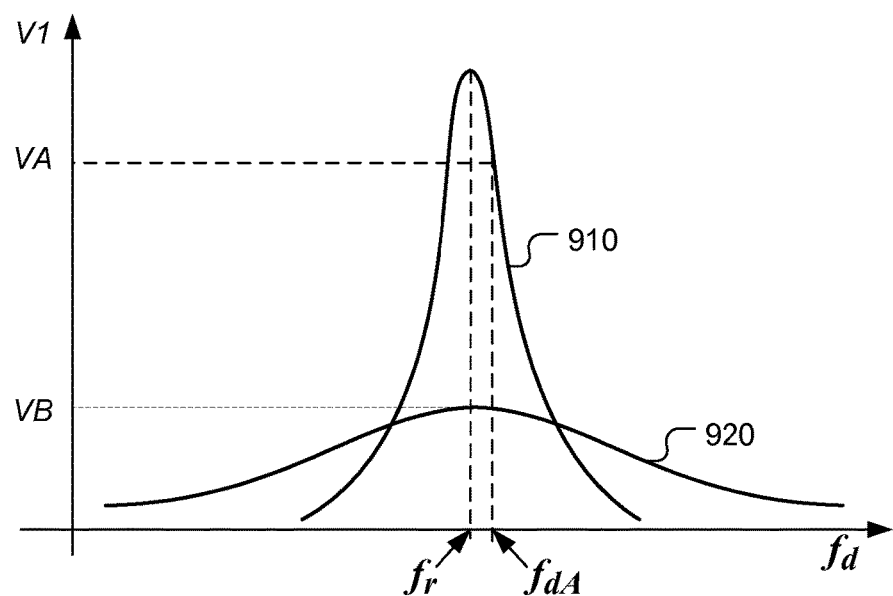
FIG. 9 illustrates an example of frequency responses of the primary resonance circuit corresponding to a correct orientation and a wrong orientation.

In FIG. 9, the primary voltage is shown as a function of drive frequency with constant drive voltage. Curve 910 corresponds to the frequency response with the capsule device docked correctly. The primary voltage is set at a value V1=VA by setting the drive frequency at $f_{dA}$. If a conductive material is inside or proximal to the primary coil (i.e., in the induced magnetic field), the quality factor Q of the primary resonance will decrease. This situation will lead to a broadening of the resonance (as illustrated by curve 920) in frequency and a reduction in the peak primary voltage. The signal source may select the drive frequency $f_r$ in an effort to maintain VA, but the primary voltage cannot exceed the value at resonance, VB. The greater the loading on the primary resonant circuit due to induced currents, the lower the Q of the driver and the lower the voltage VB. This lowered primary voltage, VB will provide the needed protection to the docking device, the capsule device or both. The quality factor Q for the resonant circuit is typical high (e.g., 10 or larger). As long as the original Q is sufficiently high so that power dissipated by inductive heating in the conductive components is a significant fraction of the resonant circuit's total loss, the reduction in Q will be sufficient to lower the primary voltage sufficiently such that the inductive heating is limited to a safe level.

The quality factor Q is maximized by minimizing resistive losses in the primary coil and primary drive circuit. Typically a Q greater than 10, with the capsule in the correct orientation, is adequate to ensure sufficient drop in voltage to avoid a heating hazard. However, a lower Q (e.g. 2) might be adequate or a higher Q (e.g. 20) might be required, depending on specifics of the system design such as the nominal drive voltage and the heat capacity and thermal resistance of the capsule device or of foreign objects that might fall into the docking system receptacle. As an example, the Q might be 20 with the capsule in the correct orientation and 12 with the capsule in the incorrect orientation. The primary voltage would drop by roughly a factor of 2 in this example when the capsule is oriented incorrectly.

While the exemplary resonant circuit illustrated in FIG. 8 corresponds to serial-connected capacitor and inductor, the capacitor and the inductor (i.e., the primary coil) may also be connected in parallel. Other resonant circuit configurations are possible utilizing the inductance of the primary combined with sources of capacitance and possible other sources of inductance. The primary could be part of an oscillator circuit oscillating at a resonant frequency determined, in part, by the primary inductance.

Figure 8B:
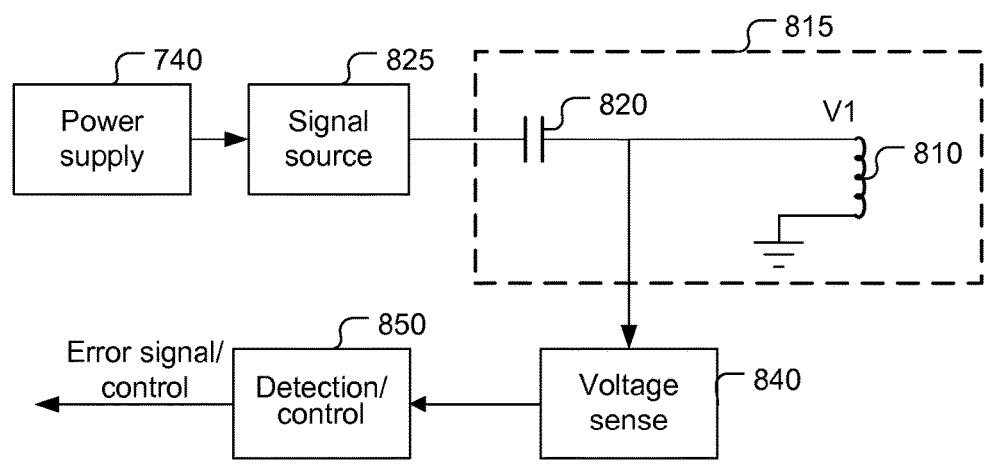

While the primary resonant circuit of FIG. 8A provides the needed protection to prevent possible damage when the capsule device is docked in a wrong orientation, it is also desirable that the system is capable of providing indication of a wrong orientation or providing additional protection. Furthermore, in some cases, the circuit configuration in FIG. 8A may not cause the quality factor Q to drop to level sufficiently low. Therefore, the resonant circuit by itself may not provide sufficient protection in case that the capsule device is docked in a wrong orientation. Accordingly, additional detection/control circuit (850) is incorporated as shown in the example of FIG. 8B, where the primary voltage is sensed by a voltage sense circuit (840) coupled to the primary coil. The voltage sense circuit may also be coupled to the signal source output before the resonant circuit (i.e., to the left side of capacitor 820). The voltage sense circuit may include a rectifier to at least partially convert the AC voltage into a DC voltage. A detection/control circuit (850) may be used to detect the voltage change and produce a control signal to other circuits to provide the needed protection. For example, the control signal may be generated by detecting when the drop in the detected voltage exceeds a threshold. When this situation occurs, the error signal is asserted. The control signal in turn may shut off the signal source (825) or open a switch (not shown in FIG. 8B) to disconnect the primary coil (810) from the resonant circuit (815). Again, for high system reliability, the voltage sense (840) and detection/control circuit (850) use hardware-based implementation, where no software or firmware is needed. The voltage sense circuit 840 may be part of the signal source 825. For example, the signal source might adjust the frequency in an effort to regulate its output voltage at a constant value, and a shift in the operating frequency may be detected by the detection/control circuit 850.

Figure 8C:
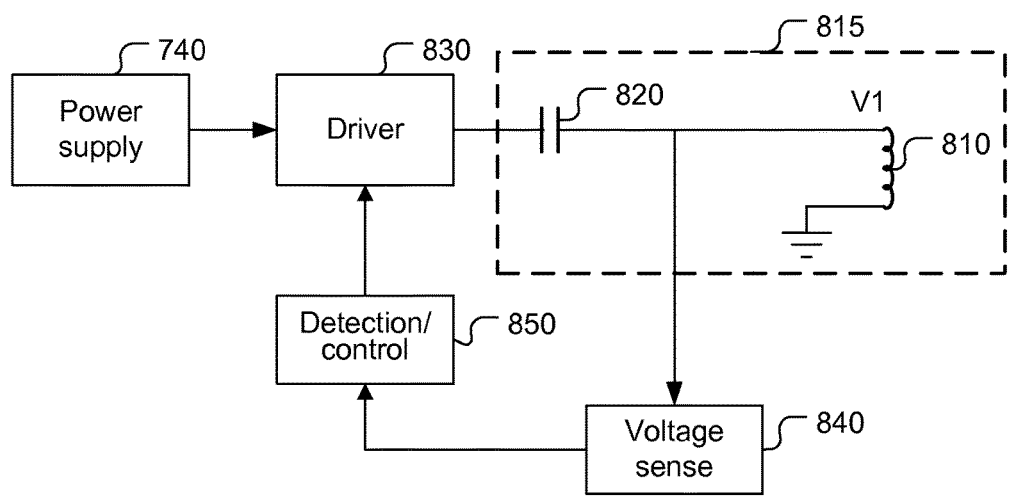

In yet another embodiment, a driver circuit (830) is used to drive the resonant circuit (815) as shown in FIG. 8C. The driver circuit (830) can be configured to provide flexible driving signals to the resonant circuit (815). For example, the driver circuit (830) can be configured to select a driving frequency $f_d$ or to provide a driving signal with a lowered voltage upon the detection of a wrong orientation as indicated by the detection/control circuit (850). Furthermore, the output of the voltage sensor may also be used as a feedback signal for the driver to control the primary voltage at a desired value during normal operation. Since the secondary voltage in the capsule device is proportional to the primary voltage, therefore the sensed voltage may also be used to derive a control signal to regulate the primary voltage as a means of stabilizing the voltage in the capsule device. This can be achieved, for example, by adjusting the drive frequency or changing the drive voltage. The voltage sense circuit 840 may be part of the driver 830. For example, the driver might adjust the frequency in an effort to regulate its output voltage at a constant value, and a shift in the operating frequency may be detected by the detection/control circuit 850.

A current sense circuit may also be used in the systems incorporating a resonant circuit as shown in FIG. 8B and FIG. 8C for foreign-object detection or for sensing a capsule with the wrong orientation. The current sense may be used to replace the voltage sense or in addition to the voltage sense. The current-sense may be more effective than voltage-sense when the change in the resonant circuit Q is small and VB is not less than VA (i.e. a change in $f_d$ towards $f_r$ prevents the primary voltage from dropping). A foreign object, especial the one with large metal part, may cause damage to the docking device if it incidentally gets into the docking device and becomes inside or proximal to the primary coil. The current sense will be able to detect the current change from the normal current that would incur when a capsule device is docked in a correct orientation. The current sense may be configured to sense the current through the primary coil (810) or the resonant circuit (815). When a driver circuit (830) is used, the current sense circuit may be configured to sense the current going into the driver circuit (830). A detection/control circuit may be used to generate error signal and/or control signal based on the sensed current.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A capsule endoscopic system comprising:
  a capsule device, wherein the capsule device comprises:
    a secondary coil;
    one or more batteries; and
    a capsule housing with an elongated shape having a first end and a second end in a longitudinal direction of the capsule device, wherein the secondary coil and said one or more batteries are sealed in the capsule housing; and
  a docking device for receiving capsule data from the capsule device and providing inductive power to the capsule device, wherein the docking device comprises:
    a primary coil to generate an alternating magnetic field, wherein the alternating magnetic field is coupled to the secondary coil to supply power to the capsule device wirelessly when the capsule device is docked in the docking device with a correct orientation, corresponding to the secondary coil being inside or proximal to the primary coil;
    a primary drive circuit coupled to the primary coil to provide an AC (alternating current) signal to the primary coil for generating the alternating magnetic field; and
    a current sense circuit coupled to the primary drive circuit or the primary coil to measure primary current flowing through the primary drive circuit or the primary coil; and
  wherein the secondary coil is disposed in proximity of the first end and said one or more batteries are disposed in proximity of the second end to cause the primary coil to be closer to the secondary coil than the battery when the capsule device is docked in the docking device in a correct orientation; and
  wherein an error signal is generated based on the primary current when the capsule device is docked in a wrong orientation corresponding to the primary coil being closer to said one or more batteries than the secondary coil.

2. The capsule endoscopic system of claim 1, wherein the docking device further comprises a detection/control circuit coupled to the current sense circuit and the error signal is generated based on the primary current using the detection/control circuit when the capsule device is docked in the wrong orientation.

3. The capsule endoscopic system of claim 2, wherein the detection/control circuit is configured to provide first control to the primary drive circuit to prevent or reduce damage to the capsule device, the docking device, or both when the error signal is asserted.

4. The capsule endoscopic system of claim 2, wherein the detection/control circuit is configured to provide a warning signal, an indication of assertion of the error signal, a message, or a combination thereof when the error signal is asserted.

5. The capsule endoscopic system of claim 2, wherein the error signal, is generated based on the primary current using only the detection/control circuit, wherein the detection/control circuit is hardware based implementation without a need for any software or firmware.

6. The capsule endoscopic system of claim 3, wherein the first control causes the primary drive circuit to be disconnected from the primary coil or from a power supply that provides power to the primary drive circuit, or causes the primary drive circuit to reduce a primary voltage across the primary coil or a duty cycle of the AC signal.

7. The capsule endoscopic system of claim 3, wherein the first control is generated based on the primary current using only the detection/control circuit, wherein the detection/control circuit is hardware-based implementation without a need for any software or firmware.

8. The capsule endoscopic system of claim 1, wherein the docking device further comprises a central processing unit (CPU) or a controller, and wherein the error signal is generated based on the primary current using the CPU or the controller when the capsule device is docked in the wrong orientation.

9. The capsule endoscopic system of claim 8, wherein the CPU or the controller is configured to provide first control to the primary drive circuit to prevent or reduce any damage to the capsule device, the docking device, or both when the error signal is asserted.

10. The capsule endoscopic system of claim 1, wherein the error signal is caused by an increase in the primary current.

* * * * *